United States Patent [19]

Delvaux

[11] 4,443,512
[45] Apr. 17, 1984

[54] ABSORBENT ARTICLE WITH DENSIFIED AREAS

[75] Inventor: Myriam Delvaux, Hannut, Belgium

[73] Assignee: Colgate-Palmolive Company, New York, N.Y.

[21] Appl. No.: 304,489

[22] Filed: Sep. 22, 1981

[51] Int. Cl.³ .......................... A61F 13/16; B32B 5/12
[52] U.S. Cl. ................................. 428/162; 604/379; 604/380; 428/171; 428/172; 428/286
[58] Field of Search ............... 428/162; 128/284, 390; 604/379, 380

[56] References Cited

U.S. PATENT DOCUMENTS

| | | | |
|---|---|---|---|
| 1,941,255 | 12/1933 | Fourness | 428/162 |
| 3,405,674 | 10/1968 | Coates et al. | 428/162 |
| 3,694,300 | 9/1972 | Small | 428/162 |
| 3,707,430 | 12/1972 | Costanza et al. | 128/290 P |
| 4,027,672 | 6/1977 | Karami | 128/284 |
| 4,322,464 | 3/1982 | Beckley | 428/175 |

Primary Examiner—George F. Lesmes
Assistant Examiner—Nawey A. B. Swisher
Attorney, Agent, or Firm—Norman Blumenkopf; Herbert S. Sylvester; Murray M. Grill

[57] ABSTRACT

An absorbent article comprising a pad of absorbent material sandwiched between a backing sheet and a top sheet. The absorbent material is a wood fluff or the like and the absorbent article is embossed on either side or both sides so that the absorbent material is compressed at the discrete areas. The balance of the absorbent material remains substantially uncompressed to form spaced densified areas and areas of less density to enhance fluid spreading characteristics and to reduce wetback.

1 Claim, 5 Drawing Figures

ABSORBENT ARTICLE WITH DENSIFIED AREAS

BACKGROUND OF THE INVENTION

1. Field of the Invention

This invention relates to an absorbent article such as a disposable diaper or sanitary napkin, and more particularly to an absorbent article which is embossed on either side or both sides as to provide for discrete areas of compressed material.

2. Description of the Prior Art

In the past absorbent articles such as disposable diapers, sanitary napkins, wound pads or the like have been manufactured by various production methods and have included embossing on one or both sides. The patterns of the embossing were generally for the purpose of enhancing rigidity of the diaper and usually occupied a substantial area of the diaper. Thus, most of the surface of the diaper was embossed and the entire absorbent pad was partially compressed. The prior embossed disposable diaper did not enhance distribution of fluid nor did it reduce wetback.

SUMMARY OF THE INVENTION

The present invention overcomes the disadvantages of the prior art diapers and provides far better liquid dispersion characteristics while reducing wetback as compared to a conventional diaper or sanitary napkin while not additional absorbent material is necessitated. In carrying out the invention absorbent material is sandwiched between a top sheet and a backing sheet. The absorbent material is of wood fluff or the like. The absorbent article is embossed on either side or on both sides so that the absorbent material is compressed to form discrete areas which are relatively highly compressed while in the other portions the absorbent material is substantially not compressed. The discrete compressed areas enhance liquid dispersion characteristics while reducing wetback.

DETAILED DESCRIPTION OF THE INVENTION

Figure 4:
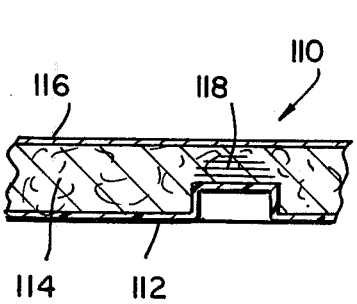
FIG. 4 is a view similar to FIG. 1 showing a modification of the invention.

Referring to the embodiment shown in FIG. 4 herein there is shown an absorbent article 110 having a backing sheet 112 of fluid impervious material such as polyethylene film or the like. Disposed on the backing sheet 112 is an absorbent material 114 such as a pad of wood fluff. Positioned above the absorbent material 114 is a top sheet 116 preferably of a non-woven hydrophobic material made of polyethelene or polypropylene fibers. In this form of the invention the backing sheet 112 is embossed to form the discrete compressed areas 118.

Figure 5:
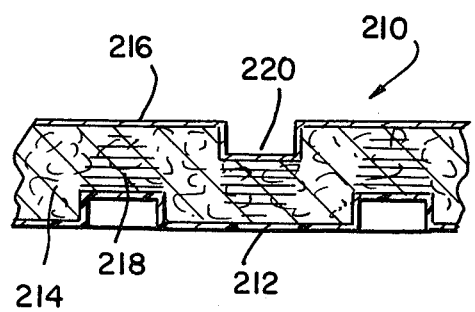
FIG. 5 is a partial sectional view showing a further modification having embossing on both sides.

In the embodiment shown in FIG. 5 and generally indicated by reference number 210 both the backing sheet 212 and top sheet 216 are embossed to form an absorbent pad 214, discrete compressed areas 218 and 220 respectively.

With continuing reference to the accompanying drawing wherein like reference numerals designate similar parts throughout the various views, reference numeral 10 generally designates an absorbent article according to the invention. The absorbent article may be a dressing, sanitary napkin, disposable diaper, or the like and as shown in the drawing the absorbent article is in the form of a disposable diaper.

The disposable diaper includes a backing sheet 12 of conventional fluid impervious material such as polyethylene film or the like.

Disposed on the backing sheet 12 is the absorbent material 14 formed of a pad of wood fluff, or the like. Positioned above the absorbent material 14 is a top sheet 16, preferably of a non-woven hydrophobic material such as polyethylene or polypropylene fibers.

The absorbent article 10 in the form of a diaper may be a contoured diaper or a box-pleated diaper with or without elasticized portions. The absorbent article is embossed at least in the crotch area of the diaper to form discrete highly compressed areas 18 as well as uncompressed areas forming the balance of the absorbent article. The discrete areas 18 underlie embossed portions 20.

Figure 1:
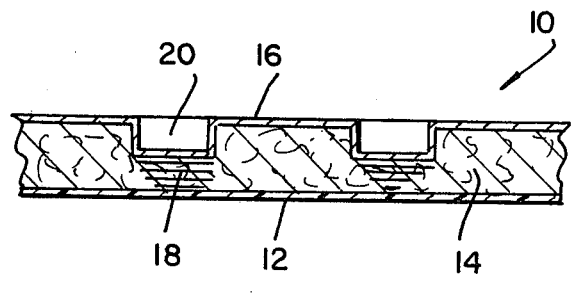
FIG. 1 is a partial sectional view through an absorbent article according to the invention.
Figures 2, 3:
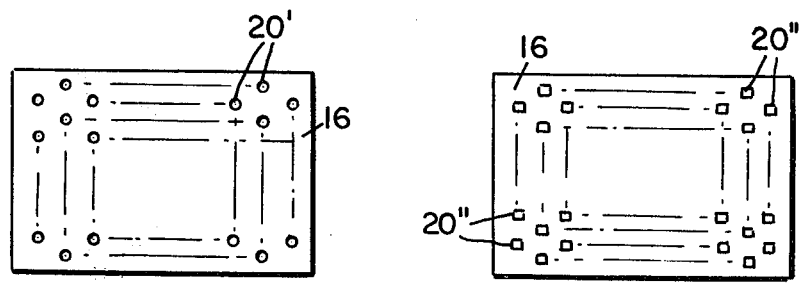
FIG. 2 is a top plan view of a portion of an absorbent article according to the invention.
FIG. 3 is a view similar to FIG. 2, but of a modified form of the invention.

As shown in FIG. 2 these areas 20' are preferably circular in cross-section or as shown in FIG. 3, these areas 20" may be rectangular of square in cross-section. Alternatively any suitable geometrical shape may be used in any convenient or desirable pattern.

In the manufacture of absorbent articles according to the invention absorbent material 14 is sprayed or otherwise applied onto a continuous sheet of film. Then the top sheet 16 is added by way of a continuous sheet of top sheet material and the assembly is then embossed by an embossing roller or plate and cut to shape.

The densified areas 18 can vary in size from 0.01 to 2 cm$^2$ and the preferred range is from 0.04 to 0.4 cm$^2$ and the optimum effects are achieved when the size of the densified area is 0.13 square centimeters.

The presence of the areas 18 of higher densities favors the spreading of liquid and improves the dryness of the diaper. Using the same amount of absorbent material, the fluid spreading ability according to the parameters of the invention increases from 8% upwardly with a fifteen percent increased fluid distribution ability at the optimum parameters set forth and fluid wetback characteristics are enhanced to an even greater degree.

The distance between the discrete areas 18 should vary between 0.1 cm to 3 cm with the preferable range being between 0.1 cm and 1 cm and a more preferable range between 0.2 cm and 0.7 cm and the optimum distance between the discrete areas 18 is 0.32 centimeters.

The density of the absorbent material which may be in the form of a pad when uncompressed and without embossing will range between 0.06 gm/cc to 0.12 gm/cc with the optimum uncompressed density being 0.09 grams per cubic centimeter.

When embossed and compressed the discrete compressed areas will range from 0.10 to 0.40 gm/cc with a preferable range between 0.15 to 0.30 gm/cc and with the optimum density being 0.22 grams per cubic centimeter.

The discrete densified areas 18 can occupy between 10% to 80% of the embossed surface of the diaper or other absorbent article. A preferable range is between 15 to 60% of the surface of the absorbent article. A more preverable range is from 20% to 30% of the surface of the absorbent article. The optimum portion of the embossed surface occupied by the discrete densified areas is 26 percent.

While the densified areas are preferably circular in shape they may be of any geometrical or non-geometrical shape and in any pattern according to choice.

One feature of the invention is that the embossed pad can be used together with an additional embossed or not embossed pad either above or below the embossed pad according to the invention.

What is claimed is:

1. An absorbent article comprising a backing sheet, an absorbent pad on said backing sheet, and a top sheet overlying said pad, said pad being of an absorbent material, said absorbent article being embossed compressing said pad so that separate discrete compressed areas are formed with the balance of the pad being substantially non-compressed, said pad when embossed including discrete areas of highly compressed absorbent material and other areas of substantially non-compressed absorbent material, said discrete areas and said other areas having the same amount of absorbent material per unit of size, said discrete areas being of 0.13 square centimeters in size, said discrete areas being spaced apart 0.32 centimeters and the density of said absorbent material in said densified areas being 0.22 grams per centimeter.

* * * * *